United States Patent
Fischer et al.

(10) Patent No.: US 11,229,476 B2
(45) Date of Patent: Jan. 25, 2022

(54) CRYOSURGICAL INSTRUMENT

(71) Applicant: Erbe Elektromedizin GmbH, Tuebingen (DE)

(72) Inventors: Klaus Fischer, Nagold (DE); Mara Szyrach, Zurich (CH); Markus Enderle, Tuebingen (DE)

(73) Assignee: ERBE ELEKTROMEDIZIN GMBH, Tübingen (DE)

( * ) Notice: Subject to any disclaimer, the term of this patent is extended or adjusted under 35 U.S.C. 154(b) by 0 days.

(21) Appl. No.: 15/638,649

(22) Filed: Jun. 30, 2017

(65) Prior Publication Data

US 2017/0360416 A1 Dec. 21, 2017

Related U.S. Application Data

(63) Continuation of application No. 13/265,789, filed as application No. PCT/EP2010/002291 on Apr. 14, 2010, now abandoned.

(30) Foreign Application Priority Data

Apr. 21, 2009 (DE) ...................... 10 2009 018 291.8

(51) Int. Cl.
*A61B 18/02* (2006.01)
*A61B 10/02* (2006.01)
(Continued)

(52) U.S. Cl.
CPC .............. *A61B 18/02* (2013.01); *A61B 10/02* (2013.01); *A61B 90/39* (2016.02);
(Continued)

(58) Field of Classification Search
CPC . A61B 10/02; A61B 18/02; A61B 2018/0212; A61B 2018/00041;
(Continued)

(56) References Cited

U.S. PATENT DOCUMENTS 3,298,371 A * 1/1967 Lee .................... A61B 18/02
219/241
3,536,075 A * 10/1970 Thomas, Jr. ......... A61B 18/02
606/23
(Continued)

FOREIGN PATENT DOCUMENTS

CA 2371776 A1 11/2000
DE 10 2007 020 582 A1 6/2008
(Continued)

*Primary Examiner* — Jennifer Pitrak McDonald
*Assistant Examiner* — Pamela M. Bays
(74) *Attorney, Agent, or Firm* — Blank Rome LLP

(57) ABSTRACT

A cryosurgical instrument, in particular a biopsy instrument for transbronchial biopsy, having an elongated instrument base body with a distal and proximal end, in relation to the operational position, a cooled section close to the distal end and which removes tissue, said section being designed such that surrounding biological material adheres thereto, by means of cryoadhesion, when said instrument is in use in the cooled state, and a security section which is provided at a distance from the tissue removal section and which comprises means for preventing or reducing the adhesion of biological material.

20 Claims, 4 Drawing Sheets

(51) Int. Cl.
*A61B 90/00* (2016.01)
*A61B 17/00* (2006.01)
*A61B 18/00* (2006.01)
*A61B 17/30* (2006.01)

(52) U.S. Cl.
CPC ........... *A61B 2017/00809* (2013.01); *A61B 2017/306* (2013.01); *A61B 2018/00005* (2013.01); *A61B 2018/00041* (2013.01); *A61B 2018/00964* (2013.01)

(58) Field of Classification Search
CPC .............. A61B 19/54; A61B 2017/306; A61B 2017/00809; A61B 2017/00292; A61B 2018/00005; A61B 2018/00964
USPC .......................................................... 606/21
See application file for complete search history.

(56) References Cited

U.S. PATENT DOCUMENTS

| | | | |
|---|---|---|---|
| 3,749,100 A * | 7/1973 | Von Der Mosel | A61N 1/0512 607/138 |
| 4,605,012 A * | 8/1986 | Ringeisen | A61N 5/04 219/690 |
| 4,938,221 A * | 7/1990 | Tuffel | A61F 7/123 606/197 |
| 5,078,713 A * | 1/1992 | Varney | A61B 18/02 606/22 |
| 5,281,215 A * | 1/1994 | Milder | A61B 18/02 606/20 |
| 5,549,600 A * | 8/1996 | Cho | A61B 18/24 606/15 |
| 5,895,403 A | 4/1999 | Collinsworth | |
| 6,224,590 B1 * | 5/2001 | Daikuzono | A61N 5/0601 606/10 |
| 6,770,070 B1 * | 8/2004 | Balbierz | A61B 10/04 600/566 |
| 2002/0045842 A1 | 4/2002 | Van Bladel et al. | |
| 2004/0024392 A1 | 2/2004 | Lewis et al. | |
| 2005/0267529 A1 | 12/2005 | Crockett et al. | |
| 2006/0025757 A1 * | 2/2006 | Heim | A61B 18/1402 606/32 |
| 2007/0250050 A1 * | 10/2007 | Lafontaine | A61B 18/02 606/21 |
| 2009/0264876 A1 * | 10/2009 | Roy | A61B 18/02 606/21 |
| 2011/0092772 A1 * | 4/2011 | Weber | A61B 1/12 600/178 |

FOREIGN PATENT DOCUMENTS

| | | |
|---|---|---|
| EP | 0 573 817 A1 | 12/1993 |
| JP | H05-76415 A | 3/1993 |
| JP | 2003-500097 A | 1/2003 |
| JP | 2003-535615 A | 12/2003 |
| JP | 2005-534460 A | 11/2005 |
| JP | 2010-512873 A | 4/2010 |
| WO | WO-0/47121 | 8/2000 |
| WO | WO-2007/026354 A1 | 3/2007 |
| WO | WO-2007/086056 A2 | 8/2007 |
| WO | WO-2008/011730 A1 | 1/2008 |
| WO | WO-2008074422 A1 | 6/2008 |
| WO | WO-2008/079696 A2 | 7/2008 |
| WO | WO-2008/156353 A1 | 12/2008 |
| WO | WO-2009/007963 A1 | 1/2009 |

* cited by examiner

CRYOSURGICAL INSTRUMENT

CROSS-REFERENCE TO RELATED APPLICATIONS

This application is a continuation of U.S. patent application Ser. No. 13/265,789, filed on Nov. 30, 2011, which is the U.S. national stage of International Application No. PCT/EP2010/002291, filed Apr. 14, 2010, which claims priority to German Application No. 10 2009 018 291.8, filed Apr. 21, 2009, the entirety of which applications are herein incorporated by reference herein.

FIELD OF THE INVENTION

Embodiments of the invention relate to a cryosurgical instrument, in particular a biopsy instrument for transbronchial biopsy.

BACKGROUND

The transbronchial biopsy under fluoroscopic control is performed as a routine diagnostic procedure of masses (e.g., bronchial carcinoma or a peripheral round lesion) and/or inflammatory interstitial pulmonary disease in the peripheral tissue of the lungs. Due to the diameter of the flexible bronchoscope, it is frequently impossible to remove a tissue sample from certain pulmonary regions that are remote from the central respiratory tract. In this case, fine forceps are advanced under fluoroscopic control (C-arm) to the region to be examined to be able to remove tissue samples in a targeted manner.

Flexible gripping forceps or cryobiopsy probes for performing this procedure have been known, for example, from European publication EP 0 573 817 A1. When the cryobiopsy technique is used for tissue removal, the probe tip (i.e., the probe head) is placed on the tissue to be treated and a tissue region—the tissue sample—is frozen to the probe head as a result of the cooling effect (Joule-Thomson effect). The tissue, or the later tissue sample, adheres to the cooled probe head and can be detached from the surrounding tissue by a short pulling motion; see WO 2008/074422.

When tissue is removed from the visualizable region of the respiratory tract (central respiratory tract), the instruments are positioned under endoscopic visualization. Contrary to this procedure, when tissue is removed from the peripheral pulmonary tissue, the instruments are positioned only indirectly under fluoroscopic control. This is associated with a higher rate of complications.

When tissue samples are taken (biopsy) from the peripheral pulmonary tissue, care must be taken so that the pulmonary tissue that is covered with an extremely thin sheath, the pleura (*Pleura visceralis*), is not punctured by the instrument used for the biopsy, e.g., by too great a mechanical force. If any damage is caused to the pleura as a result of the tissue removal, air flows out of the lung and into the pleural cavity and results in a pneumothorax that results in a reduced oxygen supply for the patient. Also, if a cryobiopsy probe is positioned too deeply, i.e., too close to the pleura, it is possible that the pleura will also freeze to the probe tip when freezing the tissue to the probe tip (probe head). Damage to the pleura may occur when the tissue adhering to the probe head is extracted.

The problem is that, for tissue removal from the peripheral tissue of the lung, the placement of the instruments just next to the pleura is very difficult and requires experienced users. Under fluoroscopic control, the user only has a 2D image for control of the probe tip. Consequently, it is difficult to also estimate depth, i.e., the third dimension.

SUMMARY

An object of the embodiments of the invention is to provide an improved instrument of the above-mentioned type, said instrument facilitating the examination by the physician and lowering the risk of complications.

In accordance with a first aspect disclosed herein, it is an essential idea to provide means on the instrument, said means preventing a direct adhesion of biological material or tissue to the distal end of the instrument, in addition to a cooled tissue grasping section located near the distal end, said tissue grasping section being designed such that, when the instrument is being used in a cooled state, surrounding biological material will adhere due to cryoadhesion. This is accomplished by a safety section provided distally from the tissue grasping section, said safety section comprising means for preventing or reducing the adhesion of biological material.

In accordance with a second, relatively independent, aspect disclosed herein, the tissue grasping section is indeed directly arranged on the distal end of the instrument; however, it is designed such that the cryoadhesion effect on a distal surface, in particular the end surface, is substantially reduced compared to that of the peripheral region.

In one embodiment in accordance with the first aspect, the safety section is designed such that it exhibits low thermal conductivity—at least in a border region of the tissue grasping section. In this case, the low thermal conductivity can be accomplished by a reduced cross-sectional surface and/or by the selection of a material that is a poor thermal conductor—at least in the border region. It should be understood that the entire safety section may consist of a material that is a poor thermal conductor or be designed with a cross-sectional area that is reduced compared to that of the tissue grasping section. Appropriate materials are, in particular, diverse plastic materials displaying their typically low thermal conductivity, and their specific selection will take into consideration the special requirements of medical technology. Mentioned here, as examples only, are silicones, polyurethanes and polyamides.

In another embodiment in accordance with the first aspect, the safety section exhibits a thermal capacity that is dimensioned such that the temperature of said safety section remains above a value at which biological material will adhere to said safety section during a short cooling duration of the tissue grasping section, in particular a duration of less than 5 seconds. In particular, said safety section may be made of a hard metal that, typically, exhibits such a high thermal capacity. Additional embodiments relating to the materials are obvious to the person skilled in the art, namely, considering the design of the instrument, specifically its cooling, and also considering the particularities of its use.

In another embodiment in accordance with the first aspect, the safety section is made of a material that reduces cryoadhesion or, at any rate, is covered by such a material, or is enclosed by a spacer of such a material. To implement this function, a coating or spacer may, in particular, consist of a hard substance that reduces cryoadhesion.

In another embodiment in accordance with the first aspect, the safety section comprises a heating device, in particular an electric heating device.

In another embodiment, a plurality of openings that are in fluid communication with a gas channel inside the instrument base body are distributed over the surface of the safety section. When the instrument is in use, the gas channel is connected to a pressure generating device that supplies a pressurized fluid (e.g., gas), said fluid being disposed to exit through the many small openings. This exiting fluid prevents—as much as is possible—the adhesion of tissue to the probe tip, i.e., in the region of the safety section.

Several of the aforementioned measures can be combined with each other, and another embodiment in accordance with the second aspect or the third aspect mentioned below can also be combined with one or more of said measures.

One embodiment in accordance with the second aspect is characterized in that cooling agents are provided in the tissue grasping section such that they only cool the peripheral section, but not the distal surface, or in that a thermal insulation can be provided between the cooling agents and the distal surface.

This causes the distal surface adjacent to the tissue grasping section to retain a clearly higher temperature than the tissue grasping section itself (during operation of the cooling device), so that, in any event, the temperature reduction is not sufficient for a serious cryoadhesion effect.

A modification of this embodiment provides that the peripheral section, but not the distal surface, be made of a material and/or have a geometric configuration and/or structure that promote the adhesion of the biological material. Indeed, in this case it is permissible that the distal surface, where no biological material is to adhere for the aforementioned reasons, assumes an essentially equally low temperature as the tissue grasping section; however, the adhesion of biological material to the latter is promoted by the adhesion-conveying coating and/or adhesion-promoting geometric configuration or surface structure such that the adhesion of material (that certainly occurs in this embodiment) is less pronounced on the distal end surface of the instrument compared therewith. It is understood that, instead of or in combination with this embodiment, it is also possible to provide the distal end surface with an anti-adhesive coating or to finish it in another way (e.g., by polishing) such that the adhesion of the material is relatively lower in that location.

A similar effect is achieved with another embodiment in accordance with the second aspect disclosed herein, wherein the tissue grasping section is provided with a plurality of openings that are in fluid communication with a gas channel on the inside the instrument base body. When the instrument is being used, the gas channel is connected with an aspirating device, so that material or tissue laterally surrounding the tissue grasping section is aspirated and, as a result of this, the cryoadhesion effect is laterally intensified. This embodiment can also be combined with a targeted adhesion-reducing embodiment of the immediate distal end of the instrument. Like the embodiment of the tissue grasping section having a plurality of small openings (that fulfill a different function in that case), said embodiment having been mentioned above, the plurality of openings in the tissue grasping section can be implemented in a simple and cost-effective manner by using a porous material for fabrication.

BRIEF DESCRIPTION OF THE DRAWINGS

Exemplary embodiments of the invention will be described in greater detail with reference to the drawings, in which.

DETAILED DESCRIPTION

Figure 1:
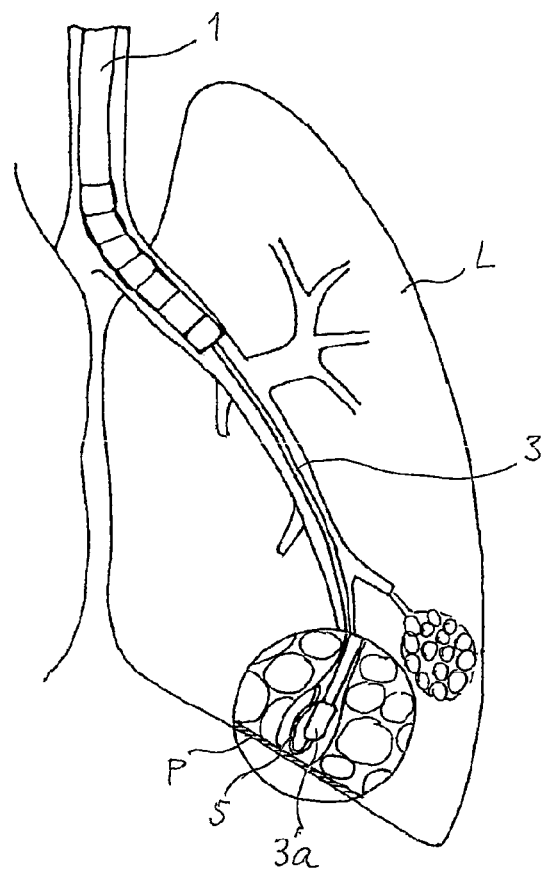
FIG. 1 is a schematic representation of a transbronchial biopsy with a flexible bronchoscope and an inserted instrument.

FIG. 1 shows a schematic representation of the longitudinal section of a lung L, with the distal end of an inserted flexible bronchoscope 1 and an inserted cryobiopsy probe 3. As can be seen from the enlarged detail in the lower part of the figure, a highly flexible guidewire 5 projects from a distal probe section 3a of the instrument 3, said guidewire 5 having been guided up to the pleura P and having been bent over due to contact with the pleura P. By providing the guidewire 5 with sufficiently low stiffness or high flexibility, as well as by using a material that can be visualized well in the applied fluoroscopic control procedure, said guidewire 5 has the function of a marker means and allows the physician handling it to stop any additional advancement of the instrument upon contact with the pleura wall, avoiding any injury to the pleura.

Figure 2:
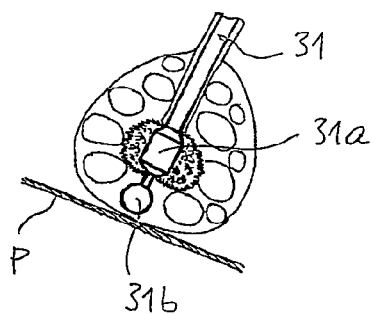
FIG. 2 is a schematic representation of a transbronchial biopsy in the bronchioli with a cryobiopsy probe.

FIG. 2 shows the distal end of another cryobiopsy probe 31 comprising a spacer (safety section) 31b on the distal end of the probe head (tissue grasping section) 31a, which spacer will not freeze when a cooling device (not shown) is activated, preventing the pleura P (*Pleura visceralis*) from freezing to the probe tip.

Figure 3:
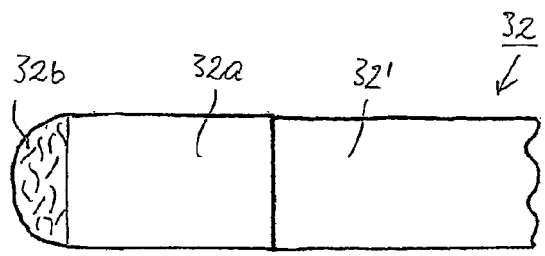
FIG. 3 is a schematic representation of a flexible cryoprobe in accordance with an embodiment of the invention.

FIG. 3 shows another cryobiopsy probe 32 comprising a flexible tube 32' of plastic material, a probe head (tissue grasping section) 32a of metal designed such that the probe head and the flexible tube have the same outside diameter. In this case, a spherical distal end surface 32b of the probe head is provided with an anti-adhesive coating that minimizes the adhesion of surrounding tissue caused by the cryoadhesion effect, compared with the remaining peripheral region of the probe 32a. A conventional anti-adhesive coating—for example, on a PTFE basis—proven in medical applications can be used.

Figure 4:
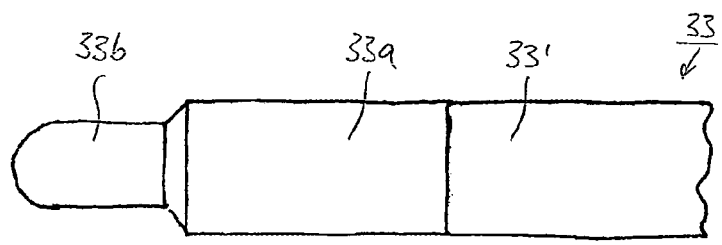
FIG. 4 is a schematic representation of a flexible cryoprobe in accordance with an embodiment of the invention.

FIG. 4 shows another cryobiopsy probe 33 comprising a flexible tube 33', a freezing device, a probe head 33a and a spacer 33b of plastic material as the probe tip, said spacer being made of plastic material exhibiting low thermal conductivity such that no tissue can freeze to the probe tip (spacer) during the freezing process.

Figure 5:
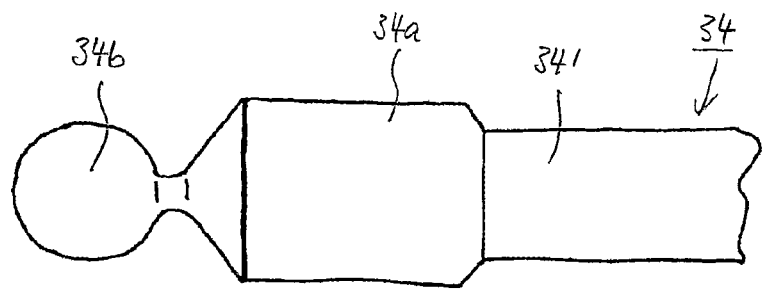
FIG. 5 is a schematic representation of a flexible cryoprobe in accordance with an embodiment of the invention.

FIG. 5 shows another cryobiopsy probe 34 comprising a flexible tube 34', a freezing device (not illustrated) in the probe head 34a, said freezing device projecting beyond the flexible tube to better freeze tissue in a lateral direction; in which case, the probe tip comprises a spacer 34b (safety section) that is a poor thermal conductor and exhibits poor thermal contact (small cross-section) with the probe head.

Figure 6:
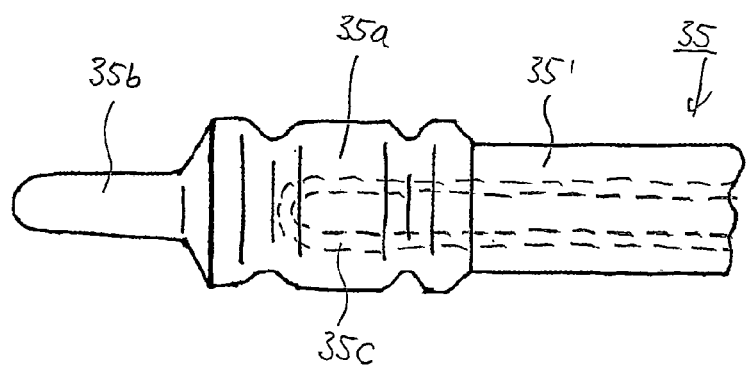
FIG. 6 is a schematic representation of a flexible cryoprobe in accordance with an embodiment of the invention.

FIG. 6 shows another cryobiopsy probe 35 comprising a flexible tube 35', a freezing device 35c in the probe head 35a, said freezing device again projecting beyond the flexible tube to better freeze tissue in a lateral direction; in which case, the geometric configuration of the surface is such that the frozen tissue adheres due to a positive connection (in the recesses), and in which case the instrument end comprises a spacer 35b.

Figure 7:
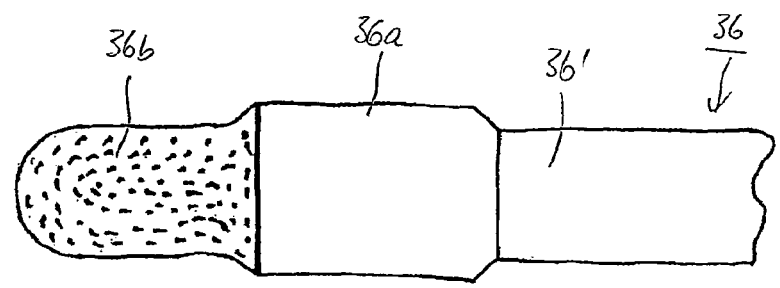
FIG. 7 is a schematic representation of a flexible cryoprobe in accordance with an embodiment of the invention.

FIG. 7 shows another cryobiopsy probe 36 comprising a flexible tube 36', a freezing device (not illustrated) in the probe head 36a, and a spacer 36b as the probe head; in which case, the spacer has many small openings and is preferably made of sintered bronze, as a result of which a gaseous medium can flow out during the freezing process to prevent any adhesion of tissue.

Figure 8:
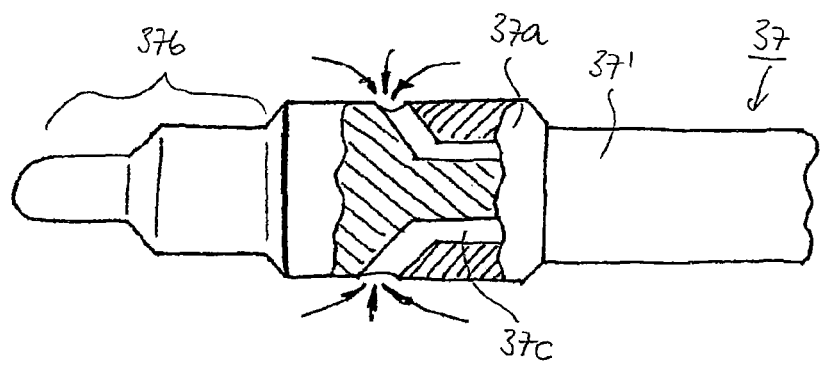
FIG. 8 is a schematic representation of a flexible cryoprobe in accordance with an embodiment of the invention.

FIG. 8 shows, partially in longitudinal section, another cryobiopsy probe 37 comprising a flexible tube 37', a freezing device (not illustrated) in the probe head, said freezing device projecting beyond the flexible tube to better freeze tissue in a lateral direction, and comprising a stepped safety section 37b, in which additional aspiration openings 37c are provided on the probe head to fixate the tissue by vacuum (negative pressure) to the probe head prior to the freezing process.

Figure 9:
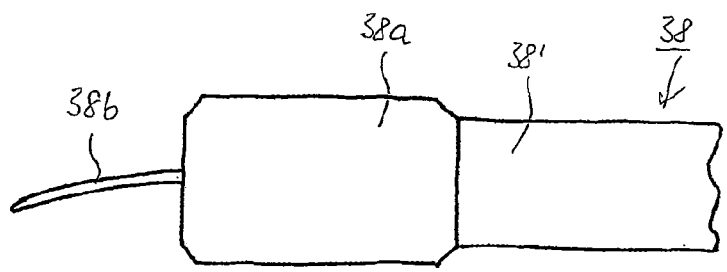
FIG. 9 is a schematic representation of a flexible cryoprobe in accordance with an embodiment of the invention.

FIG. 9 shows another cryobiopsy probe 38 comprising a flexible tube 38', a freezing device in the probe head 38a, and a thin, highly flexible, super-elastic probe tip 38b that will bend or yield with minimal resistance and that consists of a material that will be visible under fluoroscopic control (see FIG. 1).

Figure 10:
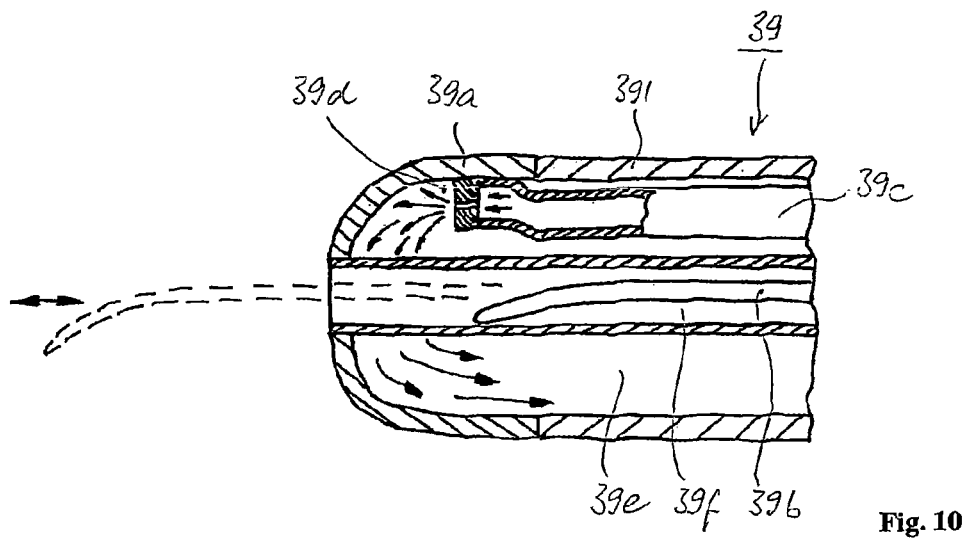
FIG. 10 is a schematic representation of a flexible cryoprobe in accordance with an embodiment of the invention.

FIG. 10 shows a representation of a longitudinal section of the distal end of another cryobiopsy probe 39 comprising a flexible tube 39', a freezing device in the probe head 39a that contains one or more gas supply lines 39c, one or more expansion openings 39d and one or more gas return lines 39e for the expanding gas, and that contains an additional channel 39f for introducing a guidewire 39b for positioning and maintaining a distance from the pleura (see FIG. 1).

The embodiments of the invention are not restricted to the examples and aspects described and illustrated herein, but can also be potentially implemented in numerous modifications that are within the framework of ordinary skill.

The invention claimed is:

1. A cryosurgical instrument comprising:
an elongated instrument base body having a distal end and a proximal end;
a cooled tissue grasping section located close to the distal end, said tissue grasping section comprising a cryoadhesive portion having a first cross-section and configured such that surrounding biological material will adhere due to cryoadhesion when the instrument is being used in a cooled state; and
a safety section provided distally from the tissue grasping section, said safety section comprising means for preventing or reducing the adhesion of biological material, wherein the tissue grasping section further comprises a border region having a cross-section that is smaller than both of the first cross-section and a cross-section of the safety section, thereby causing the border region to exhibit low thermal conductivity with respect to the cryoadhesive portion and reducing heat flow from the safety section to the cryoadhesive portion.

2. The cryosurgical instrument of claim 1, wherein said cryosurgical instrument is a biopsy instrument for performing a transbronchial biopsy.

3. The cryosurgical instrument of claim 1, further comprising a tube connected to the proximal end of the elongated instrument base body,
wherein the first cross-section is greater than a cross-section of the tube.

4. The cryosurgical instrument of claim 1, wherein the safety section exhibits a thermal capacity that is dimensioned such that the temperature of said safety section remains above a value at which biological material will adhere to said safety section during a short cooling duration of the cryoadhesive portion.

5. The cryosurgical instrument of claim 4, wherein the short cooling duration is a duration of less than 5 seconds.

6. The cryosurgical instrument of claim 1, wherein the safety section is made of a material that reduces cryoadhesion.

7. The cryosurgical instrument of claim 1, where the safety section is covered by a material that reduces cryoadhesion.

8. The cryosurgical instrument of claim 1, wherein the safety section consists of a hard substance that reduces cryoadhesion.

9. The cryosurgical instrument of claim 1, wherein the safety section comprises a heating device.

10. The cryosurgical instrument of claim 9, wherein the heating device is an electric heating device.

11. The cryosurgical instrument of claim 1, wherein the surface of the safety section has distributed over it a plurality of openings that are in fluid communication with a gas channel inside the instrument base body.

12. A cryosurgical instrument comprising:
an elongated instrument base body having a distal end and a proximal end;
a cooled tissue grasping section located close to the distal end, said tissue grasping section being configured such that surrounding biological material will adhere due to cryoadhesion when the instrument is being used in a cooled state; and
a safety section provided distally from the tissue grasping section, said safety section comprising means for preventing or reducing the adhesion of biological material, and
wherein a reduced cross-sectional surface at least in a border region of the tissue grasping section, directly adjacent to the safety section, is configured to provide low thermal conductivity between the tissue grasping section and the safety section.

13. The cryosurgical instrument of claim 12, wherein said cryosurgical instrument is a biopsy instrument for performing a transbronchial biopsy.

14. The cryosurgical instrument of claim 12, further comprising a tube connected to the proximal end of the elongated instrument base body,
wherein a cross-section of the border region is greater than a cross-section of the tube.

15. The cryosurgical instrument of claim 12, wherein the safety section exhibits a thermal capacity that is dimensioned such that the temperature of said safety section remains above a value at which biological material will adhere to said safety section during a short cooling duration of the cryosurgical instrument.

16. The cryosurgical instrument of claim 12, wherein the safety section is made of a material that reduces cryoadhesion.

17. The cryosurgical instrument of claim 12, where the safety section is covered by a material that reduces cryoadhesion.

18. The cryosurgical instrument of claim 12, wherein the safety section consists of a hard substance that reduces cryoadhesion.

19. The cryosurgical instrument of claim 12, wherein the safety section comprises a heating device.

20. A cryosurgical instrument comprising:
- an elongated instrument base body having a distal end and a proximal end;
- a safety section arranged at the distal end of the elongated instrument base body configured to prevent or reduce the adhesion of biological material; and
- a tissue grasping section arranged proximal of the safety section and configured such that surrounding biological material will adhere due to cryoadhesion when the cryosurgical instrument is used in a cooled state, the tissue grasping section having at a proximal end a first cross-section and at a distal end a second cross-section, the second cross-section being smaller than both of the first cross-section and a cross-section of the safety section, wherein the second cross-section is configured to provide low thermal conductivity thereby reducing the flow of cryoadhesion cooling to the safety section.

* * * * *